United States Patent
Hu et al.

(10) Patent No.: US 12,281,990 B2
(45) Date of Patent: Apr. 22, 2025

(54) METHOD FOR DETECTING ORGANOPHOSPHORUS PESTICIDE BY MICROFLUIDIC CHIP BASED ON FLUORESCENT SENSING FILM

(71) Applicant: Jiangsu University, Jiangsu (CN)

(72) Inventors: Xuetao Hu, Jiangsu (CN); Xiaobo Zou, Jiangsu (CN); Pei Jiang, Jiangsu (CN); Jiyong Shi, Jiangsu (CN); Xinai Zhang, Jiangsu (CN); Xiaowei Huang, Jiangsu (CN); Zhihua Li, Jiangsu (CN); Yahui Li, Jiangsu (CN); Wenting Li, Jiangsu (CN); Junjun Zhang, Jiangsu (CN)

(73) Assignee: Jiangsu University, Jiangsu (CN)

( * ) Notice: Subject to any disclaimer, the term of this patent is extended or adjusted under 35 U.S.C. 154(b) by 0 days.

(21) Appl. No.: 18/035,938

(22) PCT Filed: Feb. 28, 2022

(86) PCT No.: PCT/CN2022/078143
§ 371 (c)(1),
(2) Date: May 9, 2023

(87) PCT Pub. No.: WO2023/159532
PCT Pub. Date: Aug. 31, 2023

(65) Prior Publication Data
US 2024/0353342 A1    Oct. 24, 2024

(30) Foreign Application Priority Data
Feb. 24, 2022  (CN) .......................... 202210177211.7

(51) Int. Cl.
| | |
|---|---|
| G01N 21/84 | (2006.01) |
| B01L 3/00 | (2006.01) |
| C12Q 1/32 | (2006.01) |
| C12Q 1/46 | (2006.01) |
| G01N 21/64 | (2006.01) |

(52) U.S. Cl.
CPC .... *G01N 21/8422* (2013.01); *B01L 3/502707* (2013.01); *C12Q 1/32* (2013.01); *C12Q 1/46* (2013.01); *G01N 21/643* (2013.01); *B01L 2200/026* (2013.01); *B01L 2300/0654* (2013.01); *B01L 2300/069* (2013.01)

(58) Field of Classification Search
None
See application file for complete search history.

(56) References Cited

FOREIGN PATENT DOCUMENTS

| | | |
|---|---|---|
| CN | 2831115 | 10/2006 |
| CN | 102206485 | 10/2011 |
| CN | 104597039 | 5/2015 |
| CN | 105536899 | 5/2016 |
| CN | 109916864 | 6/2019 |
| CN | 110320187 | 10/2019 |
| CN | 110672568 | 1/2020 |
| CN | 111239118 | 6/2020 |
| CN | 111323405 | 6/2020 |
| KR | 20160006636 | 1/2016 |
| WO | 2015000243 | 1/2015 |

OTHER PUBLICATIONS

"International Search Report (Form PCT/ISA/210) of PCT/CN2022/078143," mailed on Jun. 27, 2022, pp. 1-5.
"Written Opinion of the International Searching Authority (Form PCT/ISA/237) of PCT/CN2022/078143," mailed on Jun. 27, 2022, pp. 1-4.

*Primary Examiner* — Robert J Yamasaki
(74) *Attorney, Agent, or Firm* — JCIPRNET

(57) ABSTRACT

The present invention belongs to the field of organophosphorus pesticide (OP) detection, and relates to a method for detecting an OP by a microfluidic chip based on a fluorescent sensing film. A porous fluorescent sensing film and the microfluidic chip are first constructed. The fluorescent sensing film is fabricated through layer-by-layer self-assembly of a platinum nanoparticle@oxalate-metal-organic framework (MOF) composite and a porous two-dimensional (2D) nanosheet, and has the functions of specifically detecting OPs and blocking macromolecular interferents. The microfluidic chip includes a sample channel, injection channels, reaction tanks, microfluidic channels, a detection tank, and an optical fiber channel, such that sample pretreatment and detection processes are integrated in the chip. An OP detection system is established by combining a portable constant-pressure syringe pump, a laser, a spectrometer, a signal transmitter, and a signal indicator, such that test devices are miniaturized and integrated and the OP detection is standardized.

10 Claims, 2 Drawing Sheets

METHOD FOR DETECTING ORGANOPHOSPHORUS PESTICIDE BY MICROFLUIDIC CHIP BASED ON FLUORESCENT SENSING FILM

CROSS-REFERENCE TO RELATED APPLICATION

This application is a 371 application of International PCT application serial no. PCT/CN2022/078143 filed on Feb. 28, 2022, which claims the priority benefit of China application no. 202210177211.7, filed on Feb. 24, 2022. The entirety of each of the above mentioned patent applications is hereby incorporated by reference herein and made a part of this specification.

BACKGROUND

Technical Field

The present disclosure belongs to the field of organophosphorus pesticide (OP) detection, and in particular relates to a method for detecting an OP by a microfluidic chip based on a fluorescent sensing film.

Description of Related Art

OPs refer to phosphorus-containing organic compounds, such as common OPs trichlorophone, parathion, dimethoate, and dichlorvos, which can prevent and control diseases, insects, and weeds for crops and are one of the most widely used pesticides in the cultivation of agricultural products. Detection methods for OPs mainly include instrumental analysis methods (such as gas chromatography (GC), liquid chromatography (LC), infrared (IR) spectrometry, gas chromatography-mass spectrometry (GC/MS), and ultraviolet (UV) spectroscopy) and biotechnology-based detection methods (such as enzyme inhibition, biosensor, and immunoassay). The above methods can achieve the accurate detection of OPs, but have shortcomings such as cumbersome operations or dependence on large and bulky instruments, such that the rapid and portable on-site detection of pesticide residues cannot be achieved.

With the rapid development of new nanomaterials, fluorescent nanomaterials show huge application potential in the fields of labeling, tracing, imaging, and detection due to their stable morphological structure and high luminescence efficiency. However, the current pesticide residue detection based on fluorescent nanomaterials depends on the preparation of specific nanomaterials and must be conducted in a solution, and specific molecules commonly used for detection are biological molecules such as aptamers and antigens/antibodies. Due to poor solubility or stability of a fluorescent nanomaterial in a solution, nanoparticle precipitation, fluorescence quenching, or the like may occur. The use of biological molecules has disadvantages such as high detection cost, poor detection repeatability, solution instability, and non-portability, which limit the use of fluorescent nanomaterials in on-site detection.

Compared with fluorescence detection alone, the combination of fluorescence detection with another material or another detection method can play a greater role in detection, such as the combination of a fluorescent sensing film and a microfluidic chip. A fluorescent film sensor can be fabricated to overcome shortcomings such as poor stability and easy photobleaching of fluorescent nanomaterials in solutions, and the sensor is endowed with characteristics such as portability and ease use. In order to well detect OPs, the microfluidic chip technology is used to integrate various processes such as sample pretreatment, mixing and reaction, and fluorescence detection into a chip of several square centimeters, which has advantages such as multi-functional integration, small size, and portability and is a commonly used instant detection device. The research on the current detection of OPs has not yet realized the automation, continuity, and systematization of necessary steps such as sample pretreatment, addition of specific reagents, reaction between harmful substances and specific reagents, signal acquisition, and signal processing. In addition, changes in factors such as environment and instruments will affect the stability of detection by a microfluidic chip system. Therefore, it is urgent to design a microfluidic chip system that can achieve the rapid and stable on-site detection of OPs and to establish a corresponding method for rapid on-site detection of OPs, such as to meet the requirements of rapid and highly-stable detection in harsh industrial and agricultural production environments.

SUMMARY

In view of the shortcomings of the current OP detection and due to the fact that an OP can inhibit the catalysis of acetylcholinesterase (AChE) to hydrolyze acetylcholine (ACh) and an OP concentration is correlated with an $H_2O_2$ concentration in a hydrolysate, the present disclosure constructs an $H_2O_2$ fluorescent sensing film and provides a microfluidic chip system and an OP detection method that integrate functions such as automatic sample injection, pretreatment, and detection. The present disclosure is intended to solve the problems that a microfluidic chip cannot standardize the OP detection and cannot achieve the rapid on-site detection of an OP.

The present disclosure establishes a microfluidic chip system based on a fluorescent sensing film and an OP detection method using the same, and the OP detection method includes fabrication of a specific fluorescent sensing film, construction of a microfluidic chip system, establishment of an on-site detection method, and an actual application mode. The method for detecting an OP by a microfluidic chip based on a fluorescent sensing film includes the following steps.

Step I. fabrication of a porous fluorescent sensing film, including the synthesis of a specific fluorescent material and the construction of a fluorescent sensing film thereof, which can be used for specific detection of $H_2O_2$ (a hydrolysate of ACh):

S1. synthesis of a specific oxalate@metal-organic framework (MOF) composite:

dissolving europium nitrate, pyromellitic acid, and oxalic acid in an acetonitrile-ethanol solution, stirring to obtain a mixed solution, and subjecting the mixed solution to a reaction at a specified temperature; purifying and drying to obtain an MOF powder, and redissolving the MOF powder in water to obtain an MOF (EuMOF) solution; and mixing an oxalate (TCPO) solution with the MOF solution under shaking for a specified period of time to obtain an oxalate-MOF composite (TCPO-EuMOF) solution, mixing the oxalate-MOF composite solution with a potassium chloroplatinate solution, shaking a resulting mixed solution at a specified temperature, and adding sodium borohydride to obtain a platinum nanoparticle-loaded oxalate-MOF composite (Pt@TCPO-EuMOF) solution, which is denoted as a Pt@TCPO-EuMOF solution;

S2. construction of a porous fluorescent sensing film with a surface blocking macromolecules:

cleaning a quartz substrate, soaking the quartz substrate in a polydiallyldimethylammonium chloride (PDADMAC) solution, taking the quartz substrate out, soaking the quartz substrate in the Pt@TCPO-EuMOF solution obtained in the step S1, taking the quartz substrate out, and rinsing the quartz substrate with distilled water to obtain a Pt@TCPO-EuMOF film; soaking the Pt@TCPO-EuMOF film successively in the PDADMAC solution and the Pt@TCPO-EuMOF solution, and repeating this soaking operation N times to finally form N+1 Pt@TCPO-EuMOF fluorescent sensing layers on a surface of the quartz substrate, which is denoted as a fluorescent sensing layer-modified quartz substrate;

finally, dissolving a molybdenum disulfide nanosheet, a polystyrene (PS) polymer, and PDADMAC in ethanol according to a specified ratio to obtain a mixed solution, and soaking the fluorescent sensing layer-modified quartz substrate in the mixed solution M times to form M macromolecular barrier layers on surfaces of the fluorescent sensing layers to finally obtain an OP fluorescent sensing film including the fluorescent sensing layers and the macromolecular barrier layers, which is denoted as the porous fluorescent sensing film.

Step II: design of a microfluidic chip with functions of automatic sample injection, sample pretreatment, sample-reagent mixing and reaction, and detection:

where the microfluidic chip includes a sample channel, reaction tanks, a detection tank, microfluidic channels, and an optical fiber channel; a number of the reaction tanks is n, which are successively denoted as a first reaction tank, a second reaction tank, . . . a $(n-1)_{th}$ reaction tank, and an $n_{th}$ reaction tank;

a sample inlet is formed at an end of the microfluidic chip; the sample channel is formed at one end of the first reaction tank and is connected to the sample inlet, and the other end of the first reaction tank communicates with the second reaction tank, . . . the $(n-1)_{th}$ reaction tank, and the $n_{th}$ reaction tank successively through respective ones of the microfluidic channels; an end of the $n_{th}$ reaction tank communicates with one end of the detection tank through a corresponding one of the microfluidic channels, and the optical fiber channel is formed at the other end of the detection tank; and the detection tank does not communicate with the optical fiber channel;

n injection channels are provided at a side of the microfluidic chip, which are successively denoted as a first injection channel, a second injection channel, . . . a $(n-1)_{th}$ injection channel, and an $n_{th}$ injection channel; the first injection channel communicates with the first reaction tank, the second injection channel communicates with the second reaction tank, . . . the $(n-1)_{th}$ injection channel communicates with the $(n-1)_{th}$ reaction tank, and the $n_{th}$ injection channel communicates with the $n_{th}$ reaction tank;

a fluorescent sensing film access and visual detection port is formed above the detection tank; and the n is a positive integer;

the microfluidic chip is fabricated as follows:

firstly, designing channel structures of the microfluidic chip, and with a dissolvable support material as a base material, printing a microfluidic channel model; fixing the microfluidic channel model in a container, pouring a mixture of polydimethylsiloxane (PDMS) and a curing agent thereof, and heating to a specified temperature such that the PDMS is hardened to obtain a microfluidic platform template; dissolving the microfluidic channel model in the microfluidic platform template with an organic solvent aqueous solution to obtain a microfluidic chip platform; pretreating an upper surface of the microfluidic chip platform such that microfluidic channels on the upper surface communicate with an external environment;

finally, converting a methyl group on a surface of the PDMS into a hydroxyl group by plasma technology, and sealing the upper surface of the microfluidic chip platform with a quartz substrate as an upper cover of the microfluidic chip platform; forming the fluorescent sensing film access and visual detection port in a quartz substrate zone right above the detection tank for access of the fluorescent sensing film and acquisition of a fluorescence visualization signal; and processing the optical fiber channel at a side of the detection tank near an end to finally obtain a microfluidic chip for OP detection.

Step III: establishment of an OP fluorescence colorimetric card and a quantitative detection model, specifically including the following steps:

firstly, establishing an OP microfluidic chip system, which mainly includes a constant-pressure syringe pump, syringes, connecting tubes, a microfluidic chip, a fluorescent optical fiber, a laser, a spectrometer, a signal transmitter, and a signal indicator, where the constant-pressure syringe pump is connected to the sample inlet of the microfluidic chip through a corresponding one of the connecting tubes for sample injection;

each of the syringes communicates with a respective injection channel of the injection channels through a respective one of the connecting tubes to add a reaction reagent to a respective reaction tank of the reaction tanks, where the reaction reagent is added to degrade ACh to produce $H_2O_2$;

one end of the fluorescent optical fiber is arranged in the optical fiber channel to acquire a fluorescence signal of the porous fluorescent sensing film in the detection tank, and the other end of the fluorescent optical fiber is connected to the laser and the spectrometer; and the spectrometer is configured to transmit an acquired porous fluorescent sensing film signal to the signal indicator through the signal transmitter;

secondly, preparing OP standards with h different concentration gradients, placing the porous fluorescent sensing film fabricated in the step I into the detection tank of the microfluidic chip, adding an OP standard of the OP standards by the constant-pressure syringe pump through the sample inlet, and adding the reaction reagent to the respective reaction tank through the respective injection channel by each of the syringes, such that the OP standard and the reaction reagent added are thoroughly mixed in the microfluidic channels to degrade the OP in the microfluidic channels into $H_2O_2$, and a reaction solution obtained after the reaction finally flows into the detection tank, and allowing the $H_2O_2$ in the reaction solution to react with the porous fluorescent sensing film in the detection tank for a specified period of time; after the reaction is completed, under the irradiation of a UV lamp, observing a color change of the fluorescent sensing film through the fluorescent sensing film access and visual detection port above the detection tank, acquiring pictures of the fluorescent sensing film at different organophosphorus concentrations, and combining the pictures corresponding to the different concentrations in an ascending order of the concentrations of the OP standards to obtain the OP fluorescence colorimetric card;

introducing the fluorescent optical fiber into the optical fiber channel, irradiating with exciting light, and using the spectrometer to acquire fluorescence signal intensities of the fluorescent sensing film at the different organophosphorus concentrations; and establishing a calibration curve model for OP detection according to a linear relationship between the concentrations of the OP standards and a sum of fluorescence signal intensity changes, which is denoted as y=a+bx, where x represents a concentration of an OP standard, y represents a sum of fluorescence signal intensity changes, and a and b represent a constant term and a coefficient of the equation respectively.

Step IV. OP Detection:

preparing a sample extract of a sample with reference to a sample pretreatment method in a national standard; according to the operation of detecting the OP standards in the step III, introducing the sample extract into the microfluidic chip through the sample inlet, and adding the reaction reagent through the respective injection channel; after a reaction in the detection tank is completed, observing a fluorescence color of the fluorescent sensing film with naked eyes, and according to the fluorescence colorimetric card obtained in the step III, preliminarily determining an OP concentration $n_c$ in the sample to complete the qualitative detection of the OP, where $1 \leq c \leq h$ and c is a positive integer;

further acquiring a fluorescence signal of the porous fluorescent sensing film in the detection tank through the spectrometer, substituting a sum y of fluorescence signal intensity differences into the established calibration curve model, and calculating an organophosphorus concentration X of the sample to complete the quantitative detection of the OP, where X=(a−y)/b, and a and b represent the constant term and the coefficient of the equation respectively.

Preferably, in S1 of the step I, the europium nitrate, the pyromellitic acid, the oxalic acid, and the acetonitrile-ethanol solution are in a ratio of (0.1-10) mmol:(0.05-0.5) mmol:(0.05-0.5) mmol:(50-100) mL; the acetonitrile-ethanol solution is a mixed solution of acetonitrile and ethanol in a volume ratio of (6-10):(1-4); the reaction is conducted at 100° C. to 200° C. for 12 h to 72 h; the purifying is achieved by repeatedly washing 3 to 10 times with an organic solvent, and the organic solvent includes any one selected from the group consisting of N,N-dimethylformamide (DMF), ethanol, and acetone; the drying refers to drying at 40° C. to 60° C. until a constant weight; and the MOF powder and the MOF solution have consistent optimal excitation wavelengths in a range of 500 nm to 650 nm, and optimal emission wavelengths $W_1$, $W_2$, $W_3$, . . . and $W_e$, where e is a positive integer greater than zero.

Preferably, in S1 of the step I, the oxalate solution has a mass concentration of 0.5 mg/mL to 1 mg/mL; the MOF solution has a mass concentration of 2 mg/mL to 10 mg/mL; a volume ratio of the oxalate solution to the MOF solution is 1:1; the mixed solution of the oxalate solution and the MOF solution is shaken at 30° C. to 50° C. for 12 h to 48 h; a concentration of the oxalate-MOF composite is 2 mg/mL to 10 mg/mL, a concentration of the potassium chloroplatinate is 0.3 mg/mL to 5 mg/mL, and a concentration of the sodium borohydride is 0.1 mg/mL to 1 mg/mL; the oxalate-MOF composite, the potassium chloroplatinate, and the sodium borohydride are in a volume ratio of 1:(0.1-2):(0.5-1.5); and platinum nanoparticles in the Pt@TCPO-EuMOF solution have a particle size of no greater than 50 nm.

Preferably, in S2 of the step I, the cleaning of the quartz substrate specifically refers to 3 to 8 times of ultrasonic cleaning in an ethanol solution, with 1 min to 10 min each time; the PDADMAC solution has a concentration of 0.5 g/L to 5 g/L, and the Pt@TCPO-EuMOF solution has a concentration of 0.5 mg/mL to 10 mg/mL; during the process of repeatedly soaking N times, the soaking in each of the PDADMAC solution and the Pt@TCPO-EuMOF solution is conducted for 5 min to 30 min, and N is 5 to 100; the molybdenum disulfide nanosheet, the PS polymer, the PDADMAC, and the ethanol are in a ratio of (0.1-5) mg:(0.2-2) mg:(0.01-0.1) mg:1 mL; during the process of soaking M times, the soaking in each of the solutions is conducted for 3 min to 10 min, and M is 2 to 10; and the macromolecular barrier layers on the surface of the porous fluorescent sensing film each have a pore size of 2 nm to 15 nm.

Preferably, in the step II, the channel structures of the microfluidic chip designed include the microfluidic channels, the sample channel, the reaction tanks, and the detection tank; and specific design requirements are as follows: the microfluidic channels have a total length of 5 cm to 20 cm, and a channel depth and a channel width both of 0.4 mm to 4 mm; the sample channel, the first injection channel, the second injection channel, . . . the $(n-1)_{th}$ injection channel, and the $n_{th}$ injection channel each have a length of 0.8 cm to 2 cm, and a depth and a width both of 0.4 mm to 5 mm; the first reaction tank, the second reaction tank, . . . the $(n-1)_{th}$ reaction tank, the $n_{th}$ reaction tank, and the detection tank each have a depth of 0.5 mm to 5 mm; each of the reaction tanks has an area of 0.5 cm² to 3 cm²; the detection tank has an area of 0.3 cm² to 5 cm²; and the microfluidic chip and the quartz substrate have consistent dimensions, with a length of 6 cm to 15 cm, a width of 1 cm to 10 cm, and a height of 0.5 cm to 2 cm.

Preferably, in the step II, the dissolvable support material is one selected from the group consisting of polyoxymethylene (POM), polyvinyl alcohol (PVA), and an acrylic copolymer, or a mixture of two or more thereof; a mass ratio of the PDMS to the curing agent is (7-9):(1-3); the curing agent is a silane coupling agent (SCA), which is mainly one selected from the group consisting of vinyltriamine, aminoethylpiperazine (AEP), diaminodiphenylmethane (DDM), and metaphenylenediamine, or a mixture of two or more thereof; the organic solvent aqueous solution is a mixed solution of water and an organic solvent in a volume ratio of (1-4):(6-9), and the organic solvent includes one or more selected from the group consisting of acetone, isopropyl alcohol (IPA), and nitric acid; and the heating is conducted to 65° C. to 80° C.

Preferably, in the step II, the fluorescent sensing film access and visual detection port has a pore size of 0.6 cm to 2.1 cm; the detection tank does not communicate with the optical fiber channel and is at a spacing of 0.5 cm to 1 cm from the optical fiber channel, and the optical fiber channel has a length of 1 cm to 5 cm, a width of 0.1 cm to 1 cm, and a height of 0.1 cm to 1 cm; and the microfluidic channels among the reaction tanks constitute a serpentine channel formed by the superposition of T "U" shapes, where T is a positive integer.

Preferably, in the step III, the reaction reagent includes one or more selected from the group consisting of AChE, ACh, and choline oxidase (ChOD); and the fluorescent optical fiber is specifically a 1*2 fluorescent optical fiber.

Preferably, in the step III, the reaction in the detection tank is conducted for 2 min to 10 min; the UV lamp and the exciting light each have a wavelength of 301 nm to 399 nm; the OP standards have a concentration range of 0 g/mL to 1 g/mL, and the corresponding concentrations are denoted as 0, $n_1$, $n_2$, $n_3$, . . . and $n_h$; the pictures of the fluorescent sensing film are denoted as $p_0$, $p_1$, $p_2$, $p_3$, . . . and $p_h$; the fluorescence signal intensities corresponding to the different OP standard concentrations at the wavelength $W_1$ are denoted as $I_{1,0}$, $I_{1,1}$, $I_{1,2}$, $I_{1,3}$, . . . and $I_{1,h}$, the fluorescence signal intensities corresponding to the different OP standard concentrations at the wavelength $W_2$ are denoted as $I_{2,0}$, $I_{2,1}$, $I_{2,2}$, $I_{2,3}$, . . . and $I_{2,h}$, . . . , and the fluorescence signal intensities corresponding to the different OP standard concentrations at the wavelength $W_e$ are denoted as $I_{e,0}$, $I_{e,1}$, $I_{e,2}$, $I_{e,3}$, . . . and $I_{e,h}$, where $I_{1,0}$, $I_{2,0}$, . . . and $I_{e,0}$ are corresponding fluorescence signal intensities at the OP standard concentration of 0;

the sum of fluorescence signal intensity differences is represented by y, which is denoted as $y_1$, $y_2$, $y_3$, . . . and $y_h$; and $y_1=(I_{1,1}-I_{1,0})+(I_{2,1}-I_{2,0})+ \ldots +(I_{e,1}-I_{e,0})$, $y_2=(I_{1,2}-I_{1,0})+(I_{2,2}-I_{2,0})+ \ldots +(I_{e,2}-I_{e,0})$, $y_3=(I_{1,3}-I_{1,0})+(I_{2,3}-I_{2,0})+ \ldots +(I_{e,3}-I_{e,0})$, . . . and $y_h=(I_{1,h}-I_{1,0})+(I_{2,h}-I_{2,0})+ \ldots +(I_{e,h}-I_{e,0})$, where h and e are positive integers.

Preferably, in the step IV, the reaction in the detection tank is conducted for 2 min to 10 min; and the reaction reagent includes one or more selected from the group consisting of AChE, ACh, and ChOD.

According to qualitative detection results, whether an organophosphorus content in a sample to be tested exceeds a limit standard can be rapidly determined on-site; and according to quantitative detection results, the accurate on-site determination of the sample to be tested can be achieved.

The Present Disclosure has the Following Beneficial Effects (1) In the present disclosure, a fluorescent MOF with a cage-like structure is constructed, a specific molecule oxalate is immobilized in the pore structure, and a noble metal nanoparticle is introduced to obtain a platinum nanoparticle-loaded oxalate-MOF composite. In the composite, platinum nanoparticles can catalyze a specific reaction between oxalate and $H_2O_2$, and the chemiluminescence generated by the reaction can specifically enhance a fluorescence signal of the MOF. A new chemiluminescence resonance energy transfer (CRET) system based on oxalate-$H_2O_2$ reaction product and EuMOF is constructed. The prepared fluorescent sensing material has dual functions of reaction catalysis and specific detection, and can improve the specificity and sensitivity of OP detection.

(2) In the present disclosure, a fluorescent sensing layer is fabricated through layer-by-layer assembly of the platinum nanoparticle@oxalate-MOF composite on the surface of a quartz substrate, and a load of the fluorescent sensing material is adjusted to expand an OP detection range and facilitate the use and carrying of the fluorescent material. In addition, a porous two-dimensional (2D) nanosheet material is wrapped around an outer surface of the fluorescent sensing layer to prevent macromolecules such as proteases in a reaction solution from entering the fluorescent sensing layer, such that the adverse effects of macromolecules such as proteases on a fluorescence signal are reduced, the detection accuracy is improved, and the detection limit is reduced.

(3) The present disclosure establishes a portable microfluidic chip system for OP detection by designing a microfluidic chip with functions of automatic sample injection, sample pretreatment, and sample-detection reagent mixing and reaction, such that test devices are integrated and miniaturized and the OP detection is standardized, which ultimately improves the stability and reproducibility of on-site detection.

(4) The present disclosure combines the fluorescent nano-film with the microfluidic chip. By designing the specific fluorescent film, a reaction between an OP and a specific detection reagent is sealed in the stable microfluidic chip, such that a fluorescence signal change can be observed with naked eyes to realize the rapid visual detection of an OP and a fluorescence intensity can be acquired by a portable spectrometer to realize the rapid quantitative detection of an OP.

DESCRIPTION OF THE EMBODIMENTS

Figure 1:
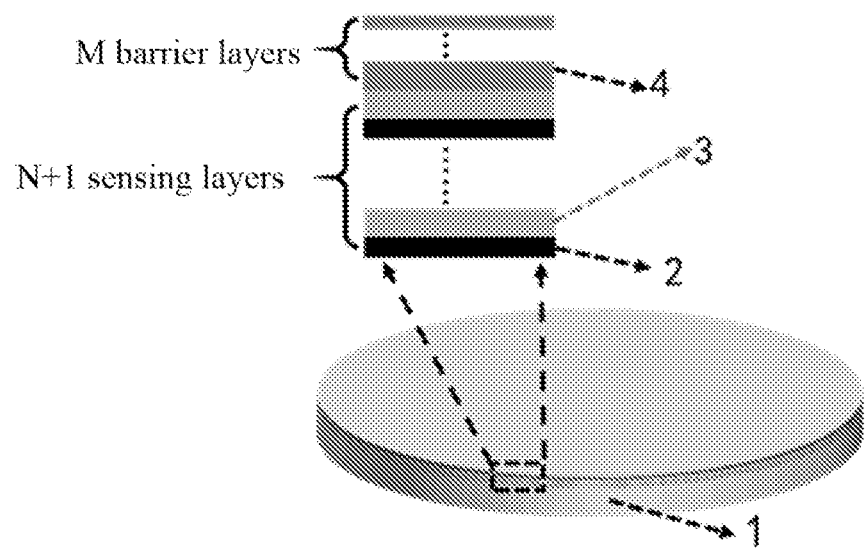
FIG. 1 is a schematic structural diagram of a porous fluorescent sensing film, where 1 represents a quartz substrate, 2 represents a PDADMAC layer, 3 represents a platinum nanoparticle@oxalate-MOF composite layer, and 4 represents a molybdenum disulfide nanosheet-PS polymer porous barrier layer.
Figure 2:
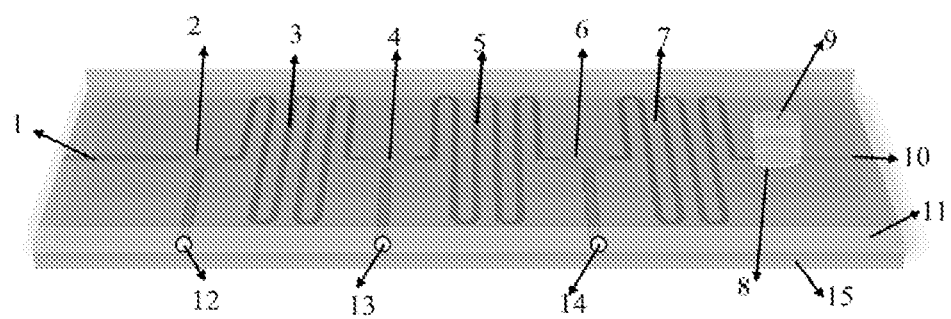
FIG. 2 is a schematic structural diagram of a microfluidic chip, where 1 represents a sample channel, 2 represents a first reaction tank, 3 represents a first microfluidic channel, 4 represents a second reaction tank, 5 represents a second microfluidic channel, 6 represents a third reaction tank, 7 represents a third microfluidic channel, 8 represents a detection tank, 9 represents a fluorescent sensing film access and visual detection port, 10 represents an optical fiber channel, 11 represents a quartz substrate, 12 represents a first injection channel, 13 represents a second injection channel, 14 represents a third injection channel, and 15 represents a microfluidic platform.

The specific implementations of the present disclosure are further described hereafter with reference to the accompanying drawings.

Example 1

A method for on-site detection of an OP based on a microfluidic chip was established, including the following steps.

Step I. Fabrication of a Fluorescent Sensing Film 1) 0.2 mmol europium nitrate, 0.8 mmol pyromellitic acid, and 0.8 mmol oxalic acid were weighed and dissolved in 100 mL of an acetonitrile-ethanol solution (in which a volume ratio of the acetonitrile to the ethanol was 6:4), and a resulting solution was stirred for 30 min, transferred to a polytetrafluoroethylene (PTFE)-lined container, and subjected to a reaction at 160° C. for 48 h in an oven; a process of adding N,N-dimethyl formamide (DMF) and centrifuging a resulting mixture was repeated 5 times for purification; and a resulting MOF (EuMOF) was dried in a drying oven at 45° C. to obtain a powder, and the powder was redissolved in water to obtain an MOF solution. According to fluorescence spectra of the MOF solution and the MOF powder, it was determined that the MOF solution and the MOF powder both had an optimal excitation wavelength of 560 nm, an excitation wavelength range of 500 nm to 650 nm, and optimal emission wavelengths respectively of 520 nm and 610 nm. Both the MOF solution and the MOF powder exhibited weak red fluorescence under the irradiation of the optimal excitation light (560 nm). The MOF was negatively charged because the ligand had a large amount of carboxyl. 10 mL of 1 mg/mL bis(2,4,6-trichlorophenyl)oxalate (TCPO) solution was mixed with 10 mL of a 5 mg/mL MOF solution, and a resulting mixture was stirred for 48 h to obtain bis(2,4,6-trichlorophenyl)oxalate-MOF composite solution. The MOF had a characteristic fluorescence peak of europium ions, the intercalated oxalate specifically reacted with $H_2O_2$ to generate an excited product, and the excited product and the MOF formed a chemical fluorescence resonance energy transfer (FRET) system. Since the absorption energy of the MOF was close to the fluorescence energy emitted by the excited product, the chemical fluorescence energy emitted by the excited product was absorbed by europium ions in the MOF, which could enhance the fluorescence of the MOF. Due to the slow and incomplete reaction between the oxalate and $H_2O_2$, 10 mL of the oxalate-MOF composite solution (3 mg/mL) was mixed with 10 mL of a potassium chloroplatinate solution (0.5 mg/mL), and then sodium borohydride (0.2 mg/mL) was added dropwise to obtain a platinum nanoparticle-loaded oxalate-MOF composite solution, which was denoted as a Pt@TCPO-EuMOF solution. In the composite, the platinum nanoparticle was introduced as a catalyst for a reaction between an oxalate and $H_2O_2$ to accelerate the speed and completion of the reaction. Results of characterization by a transmission electron microscopy (TEM) showed that the platinum nanoparticle had a particle size of no greater than 10 nm.

2) A quartz substrate with a diameter of 1 cm was taken and ultrasonically cleaned 3 times, then soaked in a PDADMAC solution with a concentration of 1 g/L for 10 min to make a surface of the quartz substrate positively charged, rinsed with distilled water, and then soaked in a 5 mg/mL platinum nanoparticle-loaded oxalate-MOF composite solution for 10 min to obtain a single Pt@TCPO-EuMOF sensing layer; the above soaking process was repeated 9 times to form 10 Pt@TCPO-EuMOF sensing layers on the surface of the substrate; and finally, 15 mg of a molybdenum disulfide nanosheet, 5 mg of a PS polymer, and 0.08 mg of PDADMAC were dissolved in 10 mL of ethanol to obtain a solution, and the quartz substrate modified with 10 Pt@TCPO-EuMOF sensing layers was soaked in the resulting solution 4 times (with 3 min each time) to form macromolecular barrier layers on the surfaces of the sensing layers. Results of characterization by the TEM showed that the molybdenum disulfide nanosheet-PS polymer barrier layers were porous and had an average pore size of 8±0.9 nm.

Step II. Fabrication of the Microfluidic Chip

A microfluidic chip with functions of automatic sample injection, sample pretreatment, sample-reagent mixing and reaction, and detection was designed.

The microfluidic chip includes a sample channel 1, a first reaction tank 2, a first microfluidic channel 3, a second reaction tank 4, a second microfluidic channel 5, a third reaction tank 6, a third microfluidic channel 7, a detection tank 8, a fluorescent sensing film access and visual detection port 9, an optical fiber channel 10, a quartz substrate 11, a first injection channel 12, a second injection channel 13, a third injection channel 14, and a microfluidic platform 15.

A sample inlet is formed at an end of the microfluidic chip; the sample inlet communicates with one end of the first reaction tank 2 through the sample channel 1, the other end of the first reaction tank 2 communicates with one end of the second reaction tank 4 through the first microfluidic channel 3, the other end of the second reaction tank 4 communicates with one end of the third reaction tank 6 through the second microfluidic channel 5, and the other end of the third reaction tank 6 communicates with the detection tank 8 through the third microfluidic channel 7; and an optical fiber channel is formed at a right side of the detection tank, and the detection tank does not communicate with the optical fiber channel.

Three injection channels are provided at a side of the microfluidic chip, which are successively denoted as a first injection channel 12, a second injection channel 13, and a third injection channel 14, where the first injection channel 12 communicates with the first reaction tank 2, the second injection channel 13 communicates with the second reaction tank 4, and the third injection channel 14 communicates with the third reaction tank 6.

A fluorescent sensing film access and visual detection port 9 is formed above the detection tank 8.

The microfluidic chip was fabricated as follows.

The Auto CAD software was used to draw a microfluidic design drawing (including 1 sample channel, 3 injection channels, 3 circular reaction tanks, 1 circular detection tank, and 3 U-shaped microfluidic channels). The 3 U-shaped microfluidic channels had a total length of 9 cm, a total width of 3 cm, and a depth of 500 μm, and the U-shaped microfluidic channels each had a width of 1 mm; and both the sample channel and each of the injection channels had a length of 1 cm and a width of 0.5 cm. A microfluidic channel template was printed with a polyoxymethylene-polyvinyl alcohol composite as a raw material, using the 3D printing technology.

The microfluidic channel template was fixed in a container with a length of 20 cm, a polydimethylsiloxane solution (which was obtained by mixing polydimethylsiloxane and a curing agent thereof in a mass ratio of 1:9) was poured, and the container was heated in an oven at 75° C. to harden the polydimethylsiloxane to obtain a microfluidic platform model; and the microfluidic channel template was dissolved with an acetic acid aqueous solution (water:acetic acid=1:9) to obtain a fluorescent microfluidic platform, and an upper surface of the microfluidic chip platform was pretreated such that the microfluidic channels on the upper surface communicate with an external environment.

Finally, methyl groups on a surface of PDMS were converted into hydroxyl groups by plasma technology, and then the upper surface of the microfluidic platform was sealed with a quartz substrate 11 as an upper cover of the microfluidic platform. The quartz substrate 11 is made of a transparent material, and thus a substance in the channels and a flow status thereof can be clearly observed through the quartz substrate 11.

A fluorescent sensing film access and visual detection port 9 was formed in a quartz substrate zone right above the detection tank 8 for access of the fluorescent sensing film and acquisition of a fluorescence visualization signal; and an optical fiber channel 10 that did not communicate with the detection tank 8 was processed at a right side of the detection tank 8 at a spacing of 0.1 cm from the detection tank 8 to finally obtain the microfluidic chip.

The sample channel 1 is an inlet channel for an OP sample, and the first injection channel 12, the second injection channel 13, and the third injection channel 14 are an AChE inlet, an ACh inlet, and a ChOD inlet, respectively.

Step III. Establishment of a Microfluidic Chip Detection Method

Figure 3:
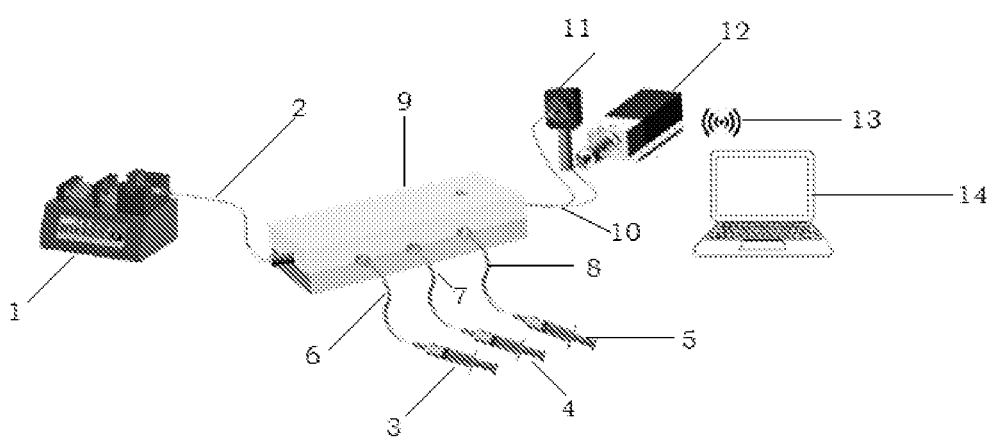
FIG. 3 is a flow chart of OP detection, where 1 represents a constant-pressure syringe pump, 2 represents a first connecting tube, 3 represents a first syringe, 4 represents a second syringe, 5 represents a third syringe, 6 represents a second connecting tube, 7 represents a third connecting tube, 8 represents a fourth connecting tube, 9 represents a microfluidic chip, 10 represents a 1*2 fluorescent optical fiber, 11 represents a laser, 12 represents a spectrometer, 13 represents a signal transmitter, and 14 represents a signal indicator.

In the present disclosure, a standard detection system was first established, as shown in FIG. 3. The standard detection system includes a constant-pressure syringe pump 1, a first connecting tube 2, a first syringe 3, a second syringe 4, a third syringe 5, a second connecting tube 6, a third connecting tube 7, a fourth connecting tube 8, a microfluidic chip 9, a 1*2 fluorescent optical fiber 10, a laser 11, a spectrometer 12, a signal transmitter 13, and a signal indicator 14.

The constant-pressure syringe pump 1 is connected to the sample inlet of the microfluidic chip 9 through the first connecting tube 2.

The first syringe 3, the second syringe 4, and the third syringe 5 are connected to the first injection channel 12, the second injection channel 13, and the third injection channel 14 of the microfluidic chip 9 respectively through the second connecting tube 6, the third connecting tube 7, and the fourth connecting tube 8.

The 1*2 fluorescent optical fiber 10 is configured to acquire a fluorescence signal of the porous fluorescent sensing film in the detection tank 8 with one end of the fluorescent optical fiber, and the other end of the fluorescent optical fiber is connected to the laser 11 and the spectrometer 12; and the spectrometer 12 is configured to transmit the acquired porous fluorescent sensing film signal to the signal indicator 14 through the signal transmitter 13.

With the established detection system, an OP detection method was established, mainly including the following steps.

(1) The fabricated fluorescent sensing film was placed in the detection tank 8, then 0.5 mL of an OP (0 ng/mL, 0.1 ng/mL, 0.5 ng/mL, 1.0 ng/mL, 3.0 ng/mL, 5.0 ng/mL, 10.0 ng/mL, 15.0 ng/mL, 20.0 ng/mL, 25.0 ng/mL, 30.0 ng/mL, 40.0 ng/mL, and 50.0 ng/mL), 0.2 mL of AChE (200 U/mL), 0.2 mL of ACh (0.5 g/mL), and 0.2 mL of ChOD (100 U/mL) were allowed to enter the microfluidic channels through the sample inlet (OP inlet), the first injection channel 12 (AChE inlet), the second injection channel 13 (ACh inlet), and the third injection channel 14 (ChOD inlet) respectively to be thoroughly mixed and react in the channels, and the resulting reaction solution finally flowed into the detection tank 8 and further incubated for 5 min.

(2) A fluorescence color of the porous fluorescent sensing film in the detection tank 8 was observed with naked eyes under the irradiation of a UV lamp (360 nm), a smartphone was used to acquire fluorescence pictures of the detection tank 8 at the different concentrations, and the fluorescence pictures were combined in an ascending order of the concentrations to obtain a fluorescence colorimetric card. It was found through observation that a red fluorescence gradually increased with the increase of the OP concentration.

(3) A portable fluorescence spectrometer 12 was used to acquire fluorescence intensities of the fluorescent sensing film in the detection tank 8, and it was found that the fluorescence signals at 520 nm and 610 nm gradually increased with the increase of the concentration; and according to a relationship between an OP concentration and an increment in fluorescence intensity (a sum of fluorescence differences at 520 nm and 610 nm, the fluorescence difference was a difference between an acquired fluorescence intensity and the fluorescence intensity at the organophosphorus concentration of 0), a calibration curve for OP detection was plotted, which had a curve equation of $y=146.89 x+64.52$ ($R^2=0.99$), where x represents an OP concentration, y represents a sum of fluorescence signal intensity changes, and a and b represent a constant term and a coefficient of the equation respectively.

Step IV. On-Site Detection of OP

The four samples of *Brassica napus, Triticum aestivum, Brassica pekinensis*, and natural water were selected. 3 g (accurate to 0.1 g) of each of the samples was weighed and added to a centrifuge tube, then 5 mL of acetone and 5 mL of phosphate buffered saline (PBS) were added, and a resulting mixture was shaken 50 times and allowed to stand for 10 min; according to the operation of detecting the organophosphorus standards in the step III, the fluorescent sensing film was placed in the detection tank 8, then 0.5 mL of a sample extract to be tested, 0.2 mL of AChE (200 U/mL), 0.2 mL of ACh (0.5 g/mL), and 0.2 mL of ChOD (100 U/mL) were allowed to enter the microfluidic channels through the OP inlet, the AChE inlet, the ACh inlet, and the ChOD inlet respectively to be thoroughly mixed and react in the channels, and the resulting reaction solution was allowed to flow into the detection tank and further incubated for 5 min; under the irradiation of a UV lamp (360 nm), a fluorescence color of the detection tank was observed with naked eyes; in contrast to the fluorescence colorimetric card, it was found that a fluorescence color of a *Brassica napus* sample extract was close to a color in the picture of fluorescence at a concentration of 5 ng/mL and thus the *Brassica napus* sample extract had a concentration of about 5 ng/mL; similarly, it was determined that a *Triticum aestivum* sample extract had a concentration of about 0.1 ng/mL, a *Brassica pekinensis* sample extract had a concentration of about 5 ng/mL, and a natural water sample extract had a concentration of about 0.1 ng/mL, thereby completing the qualitative and semi-quantitative detection of OP in the samples; and a sum of fluorescence intensity differences at 520 nm and 610 nm obtained by a fluorescence spectrometer was substituted into the established calibration curve, and organophosphorus concentrations in the *Brassica napus, Triticum aestivum, Brassica pekinensis*, and natural water samples were calculated to be 5.49 ng/mL, 0.18 ng/mL, 5.27 ng/mL, and 0.17 ng/mL, respectively, thereby completing the accurate and quantitative detection of OP. Excluding sample pretreatment, it took 15.5±1.5 min to complete the operation from the addition of a sample to the acquisition of a test result in the above method. In order to demonstrate the accuracy and efficiency of the method of the present disclosure, the same samples were tested by a national standard method, and it was found that the organophosphorus concentrations in the *Brassica napus, Triticum aestivum, Brassica pekinensis*, and natural water samples were 6.29 ng/mL, 0.58 ng/mL, 7.25 ng/mL, and 0.24 ng/mL, respectively. Excluding sample pretreatment, it took 5.1±0.3 h to complete the OP detection using the national standard method. The detection results (Table 1) of the above two methods show that the detection method of the present disclosure can achieve the accurate on-site detection of an environment and an agricultural product sample, with high detection speed and portable devices.

Table 1 Comparison of test results between the method of the present disclosure and the national standard method.

TABLE 1

Comparison of test results between the method of the present disclosure and the national standard method

| | Method of the present disclosure | | | National standard method | | |
|---|---|---|---|---|---|---|
| Sample | Concentration (ng/mL) | Standard deviation (SD) | Time consumption | Concentration (ng/mL) | SD | Time consumption |
| Brassica napus | 5.49 | 0.33 | 15 min | 6.29 | 0.68 | 5.2 h |
| Triticum aestivum | 0.28 | 0.21 | 16 min | 0.58 | 0.56 | 4.8 h |
| Brassica pekinensis | 5.27 | 0.58 | 17 min | 7.25 | 0.95 | 5.3 h |
| Natural water | 0.17 | 0.30 | 14 min | 0.24 | 0.69 | 5.1 |

Finally, it should be noted that the above embodiments are merely intended to illustrate the present disclosure, rather than to limit the technical solutions described in the present disclosure. Therefore, although the present disclosure is described in detail with reference to the above-mentioned embodiments in this specification, those of ordinary skill in the art should understand that modifications or equivalent replacements can still be made to the present disclosure. All technical solutions and improvements made without deviating from the spirit and scope of the present disclosure should be covered by the scope of the claims of the present disclosure.

What is claimed is:

1. A method for detecting an organophosphorus pesticide by a microfluidic chip based on a fluorescent sensing film, comprising the following steps:
   step I: fabrication of a porous fluorescent sensing film:
   S1: dissolving europium nitrate, pyromellitic acid, and oxalic acid in an acetonitrile-ethanol solution, stirring to obtain a mixed solution, and subjecting the mixed solution to a reaction at a specified temperature; purifying and drying to obtain a metal-organic framework powder, and redissolving the metal-organic framework powder in water to obtain a metal-organic framework solution; and
   mixing an oxalate solution with the metal-organic framework solution under shaking for a specified period of time to obtain an oxalate-metal-organic framework composite solution, mixing the oxalate-metal-organic framework composite solution with a potassium chloroplatinate solution, shaking a resulting mixed solution at a specified temperature, and adding sodium borohydride to obtain a platinum nanoparticle-loaded oxalate-metal-organic framework composite solution, which is denoted as a Pt@TCPO-EuMOF solution;
   S2: cleaning a quartz substrate, soaking the quartz substrate in a polydiallyldimethylammonium chloride solution, taking the quartz substrate out, soaking the quartz substrate in the Pt@TCPO-EuMOF solution obtained in S1, taking the quartz substrate out, and rinsing the quartz substrate with distilled water to obtain a Pt@TCPO-EuMOF film;
   soaking the Pt@TCPO-EuMOF film successively in the polydiallyldimethylammonium chloride solution and the Pt@TCPO-EuMOF solution, taking the Pt@TCPO-EuMOF film out, and rinsing the Pt@TCPO-EuMOF film with distilled water, which is a soaking cycle;
   repeating the soaking cycle N times to finally form N+1 Pt@TCPO-EuMOF fluorescent sensing layers on a surface of the quartz substrate, which is denoted as a fluorescent sensing layer-modified quartz substrate, wherein N is a positive integer;
   dissolving a molybdenum disulfide nanosheet, a polystyrene polymer, and polydiallyldimethylammonium chloride in ethanol according to a specified ratio to obtain a mixed solution, and soaking the fluorescent sensing layer-modified quartz substrate in the mixed solution M times to form M macromolecular barrier layers on surfaces of the fluorescent sensing layers to finally obtain an organophosphorus pesticide fluorescent sensing film comprising the fluorescent sensing layers and the macromolecular barrier layers, which is denoted as the porous fluorescent sensing film, wherein M is a positive integer;
   step II: fabrication of the microfluidic chip:
   wherein the microfluidic chip comprises a sample channel, reaction tanks, a detection tank, microfluidic channels, and an optical fiber channel;

a number of the reaction tanks is n, which are successively denoted as a first reaction tank, a second reaction tank, . . . a $(n-1)_{th}$ reaction tank, and an $n_{th}$ reaction tank;

a sample inlet is formed at an end of the microfluidic chip; the sample channel is formed at one end of the first reaction tank and is connected to the sample inlet, and the other end of the first reaction tank communicates with the second reaction tank, . . . the $(n-1)_{th}$ reaction tank, and the $n_{th}$ reaction tank successively through respective ones of the microfluidic channels; an end of the $n_{th}$ reaction tank communicates with one end of the detection tank through a corresponding one of the microfluidic channels, and the optical fiber channel is formed at the other end of the detection tank; and the detection tank does not communicate with the optical fiber channel;

n injection channels are provided at a side of the microfluidic chip, which are successively denoted as a first injection channel, a second injection channel, . . . a $(n-1)_{th}$ injection channel, and an $n_{th}$ injection channel; the first injection channel communicates with the first reaction tank, the second injection channel communicates with the second reaction tank, . . . the $(n-1)_{th}$ injection channel communicates with the $(n-1)_{th}$ reaction tank, and the $n_{th}$ injection channel communicates with the $n_{th}$ reaction tank;

a fluorescent sensing film access and visual detection port is formed above the detection tank; and the n is a positive integer;

the microfluidic chip is fabricated as follows:

using three-dimensional drawing software to design channel structures of the microfluidic chip, and with a dissolvable support material as a base material, printing a microfluidic channel model by a three-dimensional (3D) printer; fixing the microfluidic channel model in a container, pouring a mixture of polydimethylsiloxane and a curing agent thereof, and heating to a specified temperature such that the polydimethylsiloxane is hardened to obtain a microfluidic platform template; dissolving the microfluidic channel model in the microfluidic platform template with an organic solvent aqueous solution to obtain a microfluidic chip platform; pretreating an upper surface of the microfluidic chip platform such that the microfluidic channels on the upper surface communicate with an external environment;

converting a methyl group on a surface of the polydimethylsiloxane into a hydroxyl group by plasma technology, and sealing the upper surface of the microfluidic chip platform with a quartz substrate as an upper cover of the microfluidic chip platform;

forming the fluorescent sensing film access and visual detection port in a quartz substrate zone right above the detection tank for access of the fluorescent sensing film and acquisition of a fluorescence visualization signal; and processing the optical fiber channel at a side of the detection tank near an end to finally obtain a microfluidic chip for organophosphorus pesticide detection;

step III: establishment of an organophosphorus pesticide fluorescence colorimetric card and a quantitative detection model, specifically comprising the following steps:

establishing an organophosphorus pesticide microfluidic chip system, which mainly comprises a constant-pressure syringe pump, syringes, connecting tubes, a microfluidic chip, a fluorescent optical fiber, a laser, a spectrometer, a signal transmitter, and a signal indicator, wherein the constant-pressure syringe pump is connected to the sample inlet of the microfluidic chip through a corresponding one of the connecting tubes for sample injection;

each of the syringes communicates with a respective injection channel of the injection channels through a respective one of the connecting tubes to add a reaction reagent to a respective reaction tank of the reaction tanks, wherein the reaction reagent is added to degrade acetylcholine to produce $H_2O_2$;

one end of the fluorescent optical fiber is arranged in the optical fiber channel to acquire a fluorescence signal of the porous fluorescent sensing film in the detection tank, and the other end of the fluorescent optical fiber is connected to the laser and the spectrometer; and the spectrometer is configured to transmit an acquired porous fluorescent sensing film signal to the signal indicator through the signal transmitter;

preparing organophosphorus pesticide standards with h different concentration gradients, placing the porous fluorescent sensing film fabricated in the step I into the detection tank of the microfluidic chip, adding an organophosphorus pesticide standard of the organophosphorus pesticide standards by the constant-pressure syringe pump through the sample inlet, and adding the reaction reagent to the respective reaction tank through the respective injection channel by each of the syringes, such that the organophosphorus pesticide standard and the reaction reagent added are thoroughly mixed in the microfluidic channels to degrade the organophosphorus pesticide in the microfluidic channels into $H_2O_2$, and a reaction solution obtained after the reaction finally flows into the detection tank, and allowing the $H_2O_2$ in the reaction solution to react with the porous fluorescent sensing film in the detection tank for a specified period of time; after the reaction is completed, under the irradiation of an ultraviolet lamp, observing a color change of the fluorescent sensing film through the fluorescent sensing film access and visual detection port above the detection tank, acquiring pictures of the fluorescent sensing film at different organophosphorus concentrations, and combining the pictures corresponding to the different concentrations in an ascending order of the concentrations of the organophosphorus pesticide standards to obtain the organophosphorus pesticide fluorescence colorimetric card;

introducing the fluorescent optical fiber into the optical fiber channel, irradiating with exciting light, and using the spectrometer to acquire fluorescence signal intensities of the fluorescent sensing film at the different organophosphorus concentrations; and establishing a calibration curve model for organophosphorus pesticide detection according to a linear relationship between the concentrations of the organophosphorus pesticide standards and a sum of fluorescence signal intensity changes, which is denoted as y=a+bx, wherein x represents a concentration of an organophosphorus pesticide standard, y represents a sum of fluorescence signal intensity changes, and a and b represent a constant term and a coefficient of the equation respectively;

step IV: organophosphorus pesticide detection:

preparing a sample extract of a sample; according to the operation of detecting the organophosphorus pesticide standards in the step III, introducing the sample extract into the microfluidic chip through the sample inlet, and adding the reaction reagent through the respective injection channel; after a reaction in the detection tank is completed, observing a fluorescence color of the fluorescent sensing film with naked eyes, and according to the fluorescence colorimetric card obtained in the step III, preliminarily determining an organophosphorus pesticide concentration $n_c$ in the sample to complete the qualitative detection of the organophosphorus pesticide, wherein $1 \leq c \leq h$ and c is a positive integer, and h is the number of the organophosphorus pesticide standards in the step III;

further acquiring a fluorescence signal of the porous fluorescent sensing film in the detection tank through the spectrometer, substituting a sum y of fluorescence signal intensity differences into the established calibration curve model, and calculating an organophosphorus concentration X of the sample to complete the quantitative detection of the organophosphorus pesticide, wherein X=(a−y)/b, and a and b represent the constant term and the coefficient of the equation respectively.

2. The method for detecting the organophosphorus pesticide by the microfluidic chip based on the fluorescent sensing film according to claim 1, wherein in S1 of the step I, the europium nitrate, the pyromellitic acid, the oxalic acid, and the acetonitrile-ethanol solution are in a ratio of (0.1-10) mmol:(0.05-0.5) mmol:(0.05-0.5) mmol:(50-100) mL; the acetonitrile-ethanol solution is a mixed solution of acetonitrile and ethanol in a volume ratio of (6-10):(1-4); the reaction is conducted at 100° C. to 200° C. for 12 h to 72 h; the purifying is achieved by repeatedly washing 3 to 10 times with an organic solvent, and the organic solvent comprises any one selected from the group consisting of N,N-dimethylformamide, ethanol, and acetone;

the drying refers to drying at 40° C. to 60° C. until a constant weight; and the metal-organic framework powder and the metal-organic framework solution have consistent optimal excitation wavelengths in a range of 500 nm to 650 nm, and optimal emission wavelengths $W_1, W_2, W_3, \ldots$ and $W_e$, wherein e is a positive integer greater than zero.

3. The method for detecting the organophosphorus pesticide by the microfluidic chip based on the fluorescent sensing film according to claim 1, wherein in S1 of the step I, the oxalate solution has a mass concentration of 0.5 mg/mL to 1 mg/mL; the metal-organic framework solution has a mass concentration of 2 mg/mL to 10 mg/mL; a volume ratio of the oxalate solution to the metal-organic framework solution is 1:1; the mixed solution of the oxalate solution and the metal-organic framework solution is shaken at 30° C. to 50° C. for 12 h to 48 h; a concentration of the oxalate-metal-organic framework composite is 2 mg/mL to 10 mg/mL, a concentration of the potassium chloroplatinate is 0.3 mg/mL to 5 mg/mL, and a concentration of the sodium borohydride is 0.1 mg/mL to 1 mg/mL; the oxalate-metal-organic framework composite, the potassium chloroplatinate, and the sodium borohydride are in a volume ratio of 1:(0.1-2):(0.5-1.5); and platinum nanoparticles in the Pt@TCPO-EuMOF solution have a particle size of no greater than 50 nm.

4. The method for detecting the organophosphorus pesticide by the microfluidic chip based on the fluorescent sensing film according to claim 1, wherein in S2 of the step I, the cleaning of the quartz substrate specifically refers to 3 to 8 times of ultrasonic cleaning in an ethanol solution, with 1 min to 10 min each time; the polydiallyldimethylammonium chloride solution has a concentration of 0.5 g/L to 5 g/L, and the Pt@TCPO-EuMOF solution has a concentration of 0.5 mg/mL to 10 mg/mL; during the process of repeatedly soaking N times, the soaking in each of the polydiallyldimethylammonium chloride solution and the Pt@TCPO-EuMOF solution is conducted for 5 min to 30 min, and N is 5 to 100; the molybdenum disulfide nanosheet, the polystyrene polymer, the polydiallyldimethylammonium chloride, and the ethanol are in a ratio of (0.1-5) mg:(0.2-2) mg:(0.01-0.1) mg:1 mL; during the process of soaking M times, the soaking in each of the solutions is conducted for 3 min to 10 min, and M is 2 to 10; and the macromolecular barrier layers on the surface of the porous fluorescent sensing film each have a pore size of 2 nm to 15 nm.

5. The method for detecting the organophosphorus pesticide by the microfluidic chip based on the fluorescent sensing film according to claim 1, wherein in the step II, the channel structures of the microfluidic chip designed comprise the microfluidic channels, the sample channel, the reaction tanks, and the detection tank; and specific design requirements are as follows: the microfluidic channels have a total length of 5 cm to 20 cm, and a channel depth and a channel width both of 0.4 mm to 4 mm; the sample channel, the first injection channel, the second injection channel, . . . the $(n-1)_{th}$ injection channel, and the $n_{th}$ injection channel each have a length of 0.8 cm to 2 cm, and a depth and a width both of 0.4 mm to 5 mm; the first reaction tank, the second reaction tank, . . . the $(n-1)_{th}$ reaction tank, the $n_{th}$ reaction tank, and the detection tank each have a depth of 0.5 mm to 5 mm; each of the reaction tanks has an area of 0.5 cm² to 3 cm²; the detection tank has an area of 0.3 cm² to 5 cm²;

and the microfluidic chip and the quartz substrate have consistent dimensions, with a length of 6 cm to 15 cm, a width of 1 cm to 10 cm, and a height of 0.5 cm to 2 cm.

6. The method for detecting the organophosphorus pesticide by the microfluidic chip based on the fluorescent sensing film according to claim 1, wherein in the step II, the dissolvable support material is one selected from the group consisting of polyoxymethylene, polyvinyl alcohol, and an acrylic copolymer, or a mixture of two or more thereof; a mass ratio of the polydimethylsiloxane to the curing agent is (7-9):(1-3); the curing agent is a silane coupling agent, which is mainly one selected from the group consisting of vinyltriamine, aminoethylpiperazine, diaminodiphenylmethane, and metaphenylenediamine, or a mixture of two or more thereof; the organic solvent aqueous solution is a mixed solution of water and an organic solvent in a volume ratio of (1-4):(6-9), and the organic solvent comprises one or more selected from the group consisting of acetone, isopropyl alcohol, and nitric acid;

and the heating is conducted to 65° C. to 80° C.

7. The method for detecting the organophosphorus pesticide by the microfluidic chip based on the fluorescent sensing film according to claim 1, wherein in the step II, the fluorescent sensing film access and visual detection port has a pore size of 0.6 cm to 2.1 cm; the detection tank does not communicate with the optical fiber channel and is at a spacing of 0.5 cm to 1 cm from the optical fiber channel, and the optical fiber channel has a length of 1 cm to 5 cm, a width of 0.1 cm to 1 cm, and a height of 0.1 cm to 1 cm; and the microfluidic channels among the reaction tanks constitute a serpentine channel formed by the superposition of T "U" shapes, wherein T is a positive integer.

8. The method for detecting the organophosphorus pesticide by the microfluidic chip based on the fluorescent sensing film according to claim 1, wherein in the step III, the reaction reagent comprises one or more selected from the group consisting of acetylcholinesterase, acetylcholine, and choline oxidase;

and the fluorescent optical fiber is specifically a 1*2 fluorescent optical fiber.

9. The method for detecting the organophosphorus pesticide by the microfluidic chip based on the fluorescent sensing film according to claim 1, wherein in the step III, the reaction in the detection tank is conducted for 2 min to 10 min; the ultraviolet lamp and the exciting light each have a wavelength of 301 nm to 399 nm; the organophosphorus pesticide standards have a concentration range of 0 g/mL to 1 g/mL, and the corresponding concentrations are denoted as 0, $n_1$, $n_2$, $n_3$, ... and $n_h$; the pictures of the fluorescent sensing film are denoted as $p_0$, $p_1$, $p_2$, $p_3$, ... and $p_h$;

the fluorescence signal intensities corresponding to the different organophosphorus pesticide standard concentrations at the wavelength $W_1$ are denoted as $I_{1.0}$, $I_{1.1}$, $I_{1.2}$, $I_{1.3}$, ... and $I_{1.h}$, the fluorescence signal intensities corresponding to the different organophosphorus pesticide standard concentrations at the wavelength $W_2$ are denoted as $I_{2.0}$, $I_{2.1}$, $I_{2.2}$, $I_{2.3}$, ... and $I_{2.h}$, ..., and the fluorescence signal intensities corresponding to the different organophosphorus pesticide standard concentrations at the wavelength $W_e$ are denoted as $I_{e.0}$, $I_{e.1}$, $I_{e.2}$, $I_{e.3}$, ... and $I_{e.h}$, wherein $I_{1.0}$, $I_{2.0}$, ... and $I_{e.0}$ are corresponding fluorescence signal intensities at the organophosphorus pesticide standard concentration of 0;

the sum of fluorescence signal intensity differences is represented by y, which is denoted as $y_1$, $y_2$, $y_3$, ... and $y_h$; and $y_1 = (I_{1.1} - I_{1.0}) + (I_{2.1} - I_{2.0}) + ... + (I_{e.1} - I_{e.0})$, $y_2 = (I_{1.2} - I_{1.0}) + (I_{2.2} - I_{2.0}) + ... + (I_{e.2} - I_{e.0})$, $y_3 = (I_{1.3} - I_{1.0}) + (I_{2.3} - I_{2.0}) + ... + (I_{e.3} - I_{e.0})$, ... and $y_h = (I_{1.h} - I_{1.0}) + (I_{2.h} - I_{2.0}) + ... + (I_{e.h} - I_{e.0})$, wherein h and e are positive integers.

10. The method for detecting the organophosphorus pesticide by the microfluidic chip based on the fluorescent sensing film according to claim 1, wherein in the step IV, the reaction in the detection tank is conducted for 2 min to 10 min; and the reaction reagent comprises one or more selected from the group consisting of acetylcholinesterase, acetylcholine, and choline oxidase.

* * * * *